United States Patent [19]

Krupey

[11] Patent Number: 5,534,597
[45] Date of Patent: *Jul. 9, 1996

[54] WATER INSOLUBLE CROSS-LINKED ACID COMPOSITIONS

[75] Inventor: John Krupey, Glen Rock, N.J.

[73] Assignee: Affinity Technology, Inc., New Brunswick, N.J.

[ * ] Notice: The term of this patent shall not extend beyond the expiration date of Pat. No. 5,294,681.

[21] Appl. No.: 459,252

[22] Filed: Jun. 2, 1995

Related U.S. Application Data

[60] Division of Ser. No. 207,274, Mar. 7, 1994, Pat. No. 5,453,493, which is a continuation-in-part of Ser. No. 854,302, Apr. 30, 1992, Pat. No. 5,294,681.

[51] Int. Cl.⁶ .................................. C08F 8/30; C08F 8/12
[52] U.S. Cl. .................................. 525/327.6; 525/327.4; 525/327.8; 525/380; 525/382; 525/420; 530/350; 530/421
[58] Field of Search ............................. 525/327.6, 327.8, 525/327.4, 380

[56] References Cited

U.S. PATENT DOCUMENTS

| | | | |
|---|---|---|---|
| 2,988,539 | 6/1961 | Cohen | 525/380 |
| 3,299,184 | 1/1967 | Whitworth | 525/380 |
| 3,684,777 | 8/1972 | Field | 525/380 |

*Primary Examiner*—Fred Zitomer
*Attorney, Agent, or Firm*—Omri M. Behr; Matthew J. McDonald

[57] ABSTRACT

There is provided water insoluble cross-linked polyhydroxy polycarboxylic acid having at least two strands each having a strand skeleton of the formula:

$$-CH_2-CH-CH-CH- \\ \phantom{xxxx} | \phantom{xxx} | \phantom{xxx} | \\ \phantom{xxxx} R \phantom{xx} O=C \phantom{xx} C=O \\ \phantom{xxxxxxxxx} \backslash \phantom{x} /$$

wherein one carbonyl group of at least one maleoyl moiety thereof in each strand is covalently linked to a $$-HN.[(H)_p(CH)_z.(OH)_m].NH- \text{ moiety}$$

to provide the presence therein of at least one cross linking moiety of the formula:

$$-CH_2-CH-CH-CH- \\ | \phantom{xx} | \\ O=C \phantom{xx} C=O \\ | \phantom{xx} | \\ HN \phantom{xx} OH \\ | \\ H_p-[CH]_z-[OH]_m \\ | \\ HN \phantom{xx} OH \\ | \phantom{xx} | \\ O=C \phantom{xx} C=O \\ | \phantom{xx} | \\ -CH_2-CH-CH-CH- \\ | \\ R$$

wherein R is hydrogen or lower alkylene or lower alkoxy of 1–4 carbon atoms, or phenyl, z is an integer of 1–4, p is 0 or an integer up to z–1, m is 1 or an integer up to z, wherein the ratio of cross-links to poly (alkylene carbonic acid) strands is between about 1 and about 200 to 2. There is disclosed a method of making such polyhydroxy polycarboxylic acid as well as methods of utilizing same to remove proteins from aqueous media containing same to provide a matrix. Methods are disclosed for recovering proteins from said matrix without denaturing them and methods for recovering the polyhydroxy polycarboxylic acid from said matrix.

5 Claims, No Drawings

WATER INSOLUBLE CROSS-LINKED ACID COMPOSITIONS

RELATED APPLICATIONS

This application is a division, of application Ser. No. 08/207,274, filed Mar. 7, 1994, now U.S. Pat. No. 5,453,493 which is a CIP of Ser. No. 07/854,302, Filed: Apr. 30, 1992 now U.S. Pat. No. 5,294,681.

BACKGROUND OF THE INVENTION

1. Field Of the Invention

Removal of proteins from aqueous media by precipitation.

2. Discussion of the Prior Art

Proteins have traditionally been removed from aqueous media through use of reagents or heat. Certain solvents (chloroform, urea) denature protein and cause its precipitation. Similarly, raising the electrolyte level of a medium to a high degree by addition of salts also precipitate the protein. Further, heat not only denatures but generally coagulates protein, thus separating it from aqueous media.

There are three major drawbacks to these methods of protein removal. First, the material removed from the medium is not purely protein. Instead, when the medium contains a complex mixture of chemicals as when the medium is a cell lysate, use of these methods may cause removal of other materials in addition to protein. Second, the protein removed by these methods is generally irreversibly denatured or denaturable only by time consuming procedures such as dialysis. Third, either isolation or purification of the protein traditionally involved use of somewhat toxic solvents (phenol and/or chloroform).

3. Discussion of the Prior Art

A polymeric material described in U.S. Pat. No. 4,421,653 attempted to overcome these problems. That material, a polyethylene maleic anhydride derivative, cross-linked with diamine, however requires up to 9 volumes in solution, in order to deproteinate a single volume of blood serum. This great excess of the "deproteinizing agent" reveals its low efficiency and renders it unsuitably expensive for commercial processes. Furthermore, this matrix will precipitate proteins in the alkaline range (i.e., pH 10), thus rendering desorption of the desired protein from the matrix very difficult under mild alkaline conditions.

SUMMARY OF THE INVENTION

There is provided a group of water insoluble cross-linked polyhydroxy polycarboxylic acid compositions obtained by cross-linking a polymer of the formula:

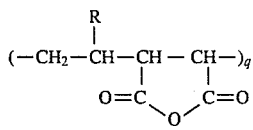

(I)

wherein R is hydrogen or lower alkylene or lower alkoxy of 1–4 carbon atoms, or phenyl, q is an integer of 7 to 10,000, with an alpha, omega diaminohydroxy alkane of the formula:

$$H_2N.[(H)_p(CH)_z.(OH)_m]NH_2 \quad (II)$$

wherein z is an integer of 1–4, p is 0 or an integer up to z–1, m is 1 or an integer up to z, and hydrolyzing the unreacted anhydride groups, wherein the ratio of the initial amount of diaminohydroxy alkane to the initial amount of poly (alkylene maleic anhydride) is between about 1 and about 200 to 1 mol/mol.

These cross-linked polyhydroxy polycarboxylic acid compositions have at least two strands each having a strand skeleton of the formula

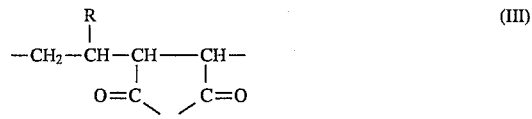

(III)

wherein one carbonyl group of at least one inter-strand maleoyl moiety thereof in each strand is covalently linked to a $$-HN.[(H)_p(CH)_z.(OH)_m].NH- \text{ moiety} \quad (IV)$$

to provide the presence therein of at least one inter-strand cross linking moiety of the formula:

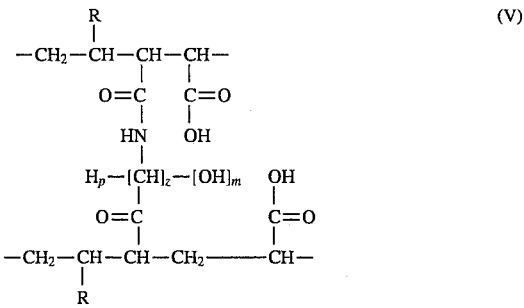

(V)

wherein R is hydrogen or lower alkylene or lower alkoxy of 1–4 carbon atoms, or phenyl, z is an integer of 1–4, p is 0 or an integer up to z–1, m is 1 or an integer up to z, wherein the ratio of cross-links to poly (alkylene carbonic acid) strands is between about 1 and about 200 to 2.

Also present in the product of the reaction of the polymer of formula I with the hydroxydiamine of formula II is the corresponding "poly maleic ester" of presumed to be of the formula VI:

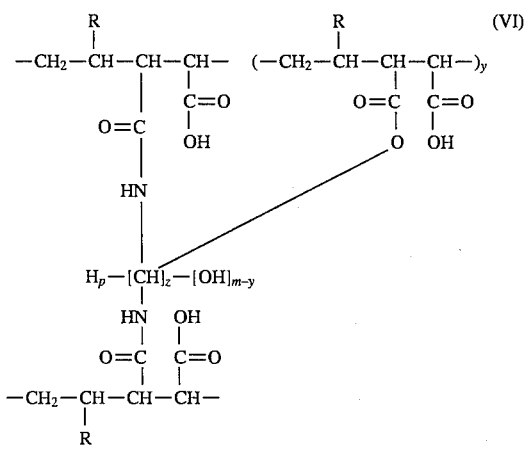

(VI)

wherein y is an integer up to m and the other values are as above.

A method disclosed herein of making the cross-linked polyhydroxy polycarboxylic acid composition entails cross-linking a polymer of Formula I with an alpha omega diaminohydroxy alkane of Formula II and hydrolyzing the unreacted anhydride groups with acid to yield a mixture of compounds of formulae V and VI.

This polymaleic ester (VI) may be readily hydrolysed back to the parent polyol (V) by mild treatment with a strong base, suitably dilute aqueous alkali at ambient temperature for several hours, preferably at least overnight. Alkaline hydrolysis of the mixture yields substantially pure formula V.

Both of these cross-linked polyhydroxy polycarboxylic acid compositions provide a method of precipitating a protein from an aqueous medium containing the same which comprises adding thereto an effective amount of such a cross-linked polyhydroxy polycarboxylic acid composition to provide a protein/polyhydroxy polycarboxylic acid composition matrix. Compounds of formula V are however substantially more efficient than the mixtures containing the corresponding esters. Suitably, the amount of polyhydroxy polycarboxylic acid composition utilized, by weight, is at least equal to the amount of protein estimated to be contained in the aqueous medium containing same. Furthermore it is desirable that the polyhydroxy polycarboxylic acid composition is utilized in an aqueous medium. In this precipitation step, it has been found useful to provide that the concentrations by weight of the protein and of the polyhydroxy polycarboxylic acid composition in their respective aqueous media have a ratio of between about 3:1 to about 1:3, most suitably when the concentrations by weight of the protein and of the cross-linked polyhydroxy polycarboxylic acid composition in their respective aqueous media are substantially equal.

The actual precipitation process is somewhat pH dependent, within fairly broad ranges, however. Thus where R is hydrogen, it is desirable that the pH of the cross-linked polyhydroxy polycarboxylic acid composition containing medium is between about 3 to about 6.2 to provide a medium after mixture of the components which does not exceed about pH 6.5. Similarly, where R is phenyl, it is desirable that the pH of the polyhydroxy polycarboxylic aid containing medium be between about 5.5 to about 7.5 to provide a medium after mixture of the components which does not exceed about pH 7.5.

After the precipitation reaction has occurred it is desirable to centrifuge the reaction mixture to recover the matrix therefrom as a pellet.

Separating the protein from the matrix without denaturing said protein may be carried out by treating said matrix with a buffer at about pH 8.6 to about 9.5. Suitably there are used about 1 to about 5 volumes of buffer, at about pH 8.6 to about 9.5, per volume of pellet of the matrix. While the invention is not limited thereto, superior results have been obtained where the buffer is a Tris buffer.

The process is also especially useful for the separation of a nucleic acid from fluids containing both protein and nucleic acid. In such cases the source of the nucleic acids or mixtures thereof is often a cell lysate suspended in aqueous guanidinium thiocyanate.

Alternatively, one may recover the cross-linked polyhydroxy polycarboxylic acid composition from the matrix to recover it by treating the matrix with an aqueous solution of sodium lauryl sulfate and then, desirably, centrifuging the reaction mixture and recovering the polyhydroxy polycarboxylic acid from or as, the residual pellet.

In this process, in which the protein is denatured, there are used about 1 to about 3 volumes of sodium lauryl sulfate of a concentration of between about 0.5 and about 2% w/w per volume of matrix residual pellet. Thereafter, it is desirable to include the further step of washing the recovered polyhydroxy polycarboxylic acid residue and resuspending it in a buffer where R=phenyl, phosphate buffered saline, suitably at pH 7.1–7.5 is used. Alternatively, where R=H, acetate buffer at pH 4–4.5 is used.

DESCRIPTION OF THE PREFERRED EMBODIMENTS

The Cross-Linked Polyhydroxy Polycarboxylic Acid Composition

The present invention encompasses a composition of matter formed by cross-linking a polymer of formula I

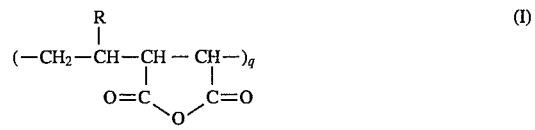

with an alpha, omega diaminohydroxy alkane of formula II:

The symbols of the atoms shown in the brackets of formula I represent the repeating unit of the polymer, and q represents the number of such united in the polymer before cross-linking the polymer with diaminohydroxy alkane. The units as represented by q may vary from 7 to 10,000.

R is hydrogen or lower alkylene or lower alkoxy of 1–4 carbon atoms, or phenyl.

It is preferred that the symbol R in formula I is hydrogen. Such a polymer, wherein q is from 120 to about 250 can be obtained from Monsanto Chemical Co., St. Louis, Mo. U.S.A, under the name ethylene-maleic acid anhydride copolymer (EMA). Also preferred is a polymer of formula I wherein R is methoxy. Such a polymer wherein q is from about 100 to about 600, can be obtained under the name Gantrez AN from GAF Corp., Chemical Division, Wayne, N.J. Also preferred is a polymer of formula I wherein R is methenyl, ethenyl, methoxy or ethoxy.

In Formula II, z is an integer of 1–4, p is 0 or an integer up to z–1, and m is 1 or an integer up to z. It is understood each (CH) group in formula II has either one or no hydroxyl groups attached thereto. The overall cross-linking moiety has at least one hydroxyl group and may have up to one hydroxyl group per (CH) group in the cross-linking chain, i.e, up to z hydroxyl groups between the two amide groups.

Alpha, omega diaminohydroxy alkanes such as those of formula II are commercially available, e.g., 1,3-diamino-2-hydroxy-propane (Aldrich Chemical Co., Milwaukee, Wis).

Any anhydride groups remaining in the water insoluble cross-linked polyhydroxy polycarboxylic acid are hydrolyzed.

In the water insoluble cross-linked polyhydroxy polycarboxylic acid composition, the ratio of the initially charged diaminohydroxy alkane to the initially charged poly(alkylene maleic anhydride)is between about 1 and about 200 to 1 mol/mol.

In a further embodiment, the water insoluble cross-linked polyhydroxy polycarboxylic acid has at least two strands, each having a strand skeleton of formula III:

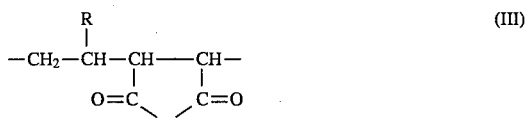

wherein one carbonyl group of at least one maleoyl moiety thereof in each strand is covalently linked to a alpha, omega diaminohydroxy alkyl of formula IV:

—HN.[(H)$_p$(CH)$_z$.(OH)$_m$].NH— moiety     (IV)

This provides the presence therein of at least one cross-linking moiety of the formula V:

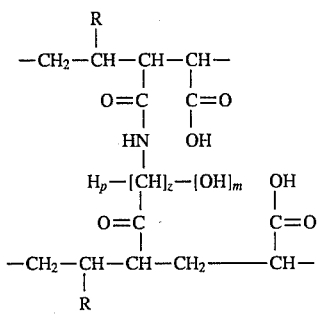

The symbols R, p, z and m have the same values as in formulae I and II above respectively. The ratio of cross-links to poly(alkylene carbonic acid) strands in formula V is between about 1 and about 200 to 2 (1:2 through 200:2).

Method of Making Cross-Linked Polyhydroxy Polycarboxylic Acid Composition

In a further embodiment of the invention, the method of making the water insoluble cross-linked polyhydroxy polycarboxylic acid composition entails cross-linking a polymer of formula I with an alpha, omega diaminohydroxy alkane of formula II, and hydrolyzing the unreacted anhydride groups. A volume of poly(alkylene maleic anhydride) conforming to formula I is added to a reacting vessel. A volume of alpha, omega diaminohydroxy alkane conforming to formula II is also added to the reacting vessel. The ratio of the initially charged diaminohydroxy alkane to the initially charged poly(alkylene maleic anhydride) is between about 1 and about 200 to 1 mol/mol.

This is performed typically by mixing the polymer of formula I with an alpha, omega diaminohydroxy alkane in water or in an organic solvent such as acetone for 1–5 hours followed by 0–24 hours during which the reaction mixture is allowed to stand at room temperature. The reaction may be carried out at atmospheric pressure at room temperature or elevated temperature. The diaminohydroxy alkane converts by the cross-linking reaction the anhydride groups of the polymer of formula 1 into carboxy and amide groups. Contemporaneously, in amounts depending on the reaction conditions utilized, some of the hydroxyl groups in the linking hydroxydiamido chain are esterified by further reaction with anhydride to form the corresponding "poly maleic ester" (VI). At some time during or after this reaction, unreacted anhydride groups are converted into carboxy groups by hydrolysis in an aqueous medium (as by addition an acid solution to lower pH). While the mixture containing the esterified moieties (VI) is operative for the removal of proteins, it is preferred to hydrolyse these ester moieties by digestions in aqueous alkali, suitably dilute alkali for example 0.05 to 0.5 N aqueous sodium hydroxide, suitably at ambient temperature for from about 12 to about 36 hours to yield the pure polyhydroxy compound (V).

After the reaction is completed, an aqueous phase may be added to the mixture, the organic phase removed conventionally as by evaporation under vacuum, and the residue dried at room temperature to provide the water insoluble cross-linked polyhydroxy polycarboxylic acid.

Method of Protein Removal Using the Water Insoluble Cross-Linked Polyhydroxy Polycarboxylic Acid Composition A further embodiment of the invention is a method of precipitating a protein from an aqueous medium containing the same which comprises adding thereto an effective amount of the cross-linked polyhydroxy polycarboxylic acid composition to provide a protein/polyhydroxy polycarboxylic acid composition matrix.

The aqueous medium may be a diluted or undiluted biological fluid containing protein desired to be removed and includes such fluids as whole blood, plasma, sera, lymph, bile, urine, liquid, spinal fluid, sputum, sweat and the like, as well as stool excretions. It is possible also to use fluid preparations of human or other animal tissue such as skeletal muscle, heart, kidney, lungs, brain, including cell culture extracts or milk or microbiological culture fluids or plant extracts. The preferred biological fluids are human blood and bacterial cell lysates.

The water insoluble cross-linked polyhydroxy polycarboxylic acid composition may be added to the aqueous medium containing protein in the form of an emulsion, a suspension, a solution or a dry powder.

The ratio of the cross-linked polyhydroxy polycarboxylic acid composition to the biological fluid can vary according to the degree of deproteinization desired. The optimum ratio is, however, preferably determined in each case having regard to the concentration of proteins, the nature and the concentration of the substance to be purified, the temperature, the pH value and the ion concentration. The temperature and the pH value are, in principle, not critical. However, the temperature generally lies between 0° and 100° C., preferably between 4° C., but not above 60° C. as substantial irreversible protein denaturation occurs above this temperature.

It is noted that the efficiency of protein precipitation by the cross-linked polyhydroxy polycarboxylic acid composition appears to increase at higher temperatures. In other words, less cross-linked polyhydroxy polycarboxylic acid composition is required to remove 90% of protein from a sample solution at 60° C. then from an otherwise identical protein solution at 30° C.

The pH value in the aqueous medium containing protein, after addition of the water insoluble cross-linked polyhydroxy polycarboxylic acid does not exceed about pH 7.5, or preferably about pH 6.5.

The concentrations by weight of the protein and of polyhydroxy polycarboxylic acid and their respective aqueous media suitably have a ratio of between about 3:1 to about 1:3.

The amount of cross-linked polyhydroxy polycarboxylic acid composition utilized, by weight is generally at least equal to the amount of protein estimated to be contained in the aqueous medium containing same.

When the water insoluble cross-linked polyhydroxy polycarboxylic acid composition is suspended in its own aqueous medium prior to being added to the protein-containing aqueous medium, and R is H, the pH of the polyhydroxy polycarboxylic acid composition containing medium is between about 3 to about 5, to provided a medium after mixture of the components which does not exceed about pH 6.5.

Alternatively, when R is phenyl, the pH of the cross-linked polyhydroxy polycarboxylic acid composition containing medium is between about 5.5 to about 7.5 to provide a medium after mixture of the components which does not exceed about pH 7.5.

The degree of the deproteinization of the aqueous medium depends on the density of the reactive groups in the cross-linked polyhydroxy polycarboxylic acid composition agent. The density of the reactive groups is not critical for the operability of the invention provided that an adequate quantity thereof is present in order to guarantee the bonding of a sufficient quantity.

Typically, the cross-linked polyhydroxy polycarboxylic acid composition agent is added to the biological fluid and after a fixed time (generally 5 to 15 minutes) of intensive contact (e.g. by stirring or inversion followed by standing). The resulting water insoluble phase comprising a matrix of cross-linked polyhydroxy polycarboxylic acid composition and protein which has associated with the protein is removed. This removal can be carried out by any conventional method customary for phase separation (e.g. centrifugation, filtration or sedimentation). The removal of the water insoluble phase provides, thereby, a deproteinized supernatant.

Where the removal of the water insoluble phase is by centrifugation, centrifugation should be performed at from about 5 to 100,000 g's for from 0.2 to 10 hours or settling under unit gravity. Ultracentrifugation speeds may be used advantageously because the resulting pellet is so tightly packed no fines are lost when the supernatant is decanted.

The present method of protein removal may also be used to extract a substance, which is precipitated by the cross-linked polyhydroxy polycarboxylic acid composition or is precipitated therewith by a suitable treatment such as, for example, by the use of special buffer solutions or other extraction agents such as surfactants. Removal of this substance may be for preparative or analytic purposes. If buffer solutions are used to separate the protein from the matrix, it is accomplished by stirring, grinding and/agitating said matrix with a buffer at about pH 8.6 to about 9.5 for from 10–60 minutes. There are used about 1 to about 5 volumes of buffer, at about pH 8.6 to about 9.5, per volume of pellet of the matrix. The buffer may suitably be Tris buffer. When the matrix is treated a surfactant extraction agent, (suitably sodium lauryl sulfate) there may be used about 1 to about 3 volumes of sodium lauryl sulfate of a concentration at between about 0.5 and about 2% w/w per volume of matrix residual pellet.

When one performs the above steps and recovers the water insoluble crosslinked polyhydroxy polycarboxylic acid composition from the precipitated matrix, the polyhydroxy polycarboxylic acid composition may be washed and resuspended in phosphate buffered saline of pH 7.1–7.5. Thus, a further embodiment of the method of precipitating a protein is to perform the further step of washing the said recovered cross-linked polyhydroxy polycarboxylic acid composition and resuspending same in phosphate buffered saline, preferably having pH 7.1–7.5.

The method of precipitating protein is especially useful when the protein is present in an aqueous medium with a nucleic acid or mixtures thereof. This is frequently the case when the source of nucleic acid or mixtures thereof is a cell lysate suspended in aqueous guanidium thiocyanate.

The deproteinized supernatant (the deproteinized fluid remaining behind after deproteinization) can be further processed in any manner. For preparative purposes (e.g. for the purification of peptides, glycoproteins, steroids, lipolds, nucleic acids, enzymes, hormones, vitamins, viruses, polysaccharides or alkaloids) further purification steps can, for example, be carried out. In this case, there are suitable, in particular, chromatography (e.g. ion exchange, Sephadex, affinity or adsorption chromatography), filtration, (e.g. ultra-filtration), electrophoresis (e.g. block, disc or carrier-free electrophoresis), isoelectric focusing and selective precipitation.

Without in any way restricting the scope of present invention, Applicant wishes to state his understanding of the present invention, namely the mechanism by which the cross-linked polyhydroxy polycarboxylic acid composition removes protein from an aqueous medium. Precipitability is a function of solubility in an aqueous medium. Solubility in turn is a function at least in part of the degree of a protein's hydrophobicity. All proteins have at least some hydrophobic portions of their surface exposed to the aqueous medium. Applicant believes his cross-linked polyhydroxy polycarboxylic acid composition permits the hydrophobic portions of different protein molecules to approach one another and aggregate to such a degree that the proteins eventually precipitate. (This appears to be corroborated by the increased protein removal efficiency of the cross-linked polyhydroxy polycarboxylic acid composition from solutions at higher temperatures. By contrast, where protein precipitation is caused by other phenomena, e.g., association/dissociation, protein precipitation is seen to fall off as temperature rises).

Before this can happen, the cross-linked polyhydroxy polycarboxylic acid composition associates with one or more protein molecules by non-covalent interaction, such as electrical charge attraction. (The cross-linked polyhydroxy polycarboxylic acid composition has numerous negative charges which can interact with the partial positive charges present in several points in all protein molecules, e.g. at arginine residues). The local ordering of water imposed by the surface hydrophobic groups is thermodynamically unfavored. Bound water may be released when these hydrophobic groups which are apolar, interact with one another and aggregate. Thus, when two or more proteins which have interacted with the flexible cross-linked polyhydroxy polycarboxylic acid composition like beads on a string, the composition-string can then enfold such apolar portions of different protein-beads may aggregate. When the number or size of aggregated protein molecules is large enough, the protein-composition complex precipitates.

The following examples are meant to illustrate the present invention and do not restrict the invention in any respect.

EXAMPLE 1

Preparation of a Water-Insoluble Precipitating Agent(Mixture of Partially Esterified Material (VI)and Deesterified Material (V)

One hundred grams (0.063 moles) of styrene maleic anhydride copolymer (SAM® Resin 1000A) obtained from Atochem Inc,, Malvern, Pa. is dissolved in 1L of acetone. To this solution is added a second solution containing 17.5 g. (0.194 moles) of 1,3-diamino-2hydroxy propane (Aldrich Chemical Company, Milwaukee, Wis.) in 1L of acetone at a rate of 5.0 ml/min. with constant stirring for a period of 3.5 h.

The reaction mixture is then allowed to stand for 12 hours at room temperature. After completion of the reaction, 3 L of water is added with stirring and then the polymer is allowed to settle under unit gravity. The aqueous organic phase is removed by decantation. The cross-linked polymer is suspended in 1L of $H_2O$ and ground for 1 minute using a Gifford Wood homogenizer (medium setting). The pH of the suspension is then adjusted to 1.5 by the addition of hydrochloric acid. After 1 hour, the pH is adjusted to 9.0 with sodium hydroxide and the mixture stirred for 30 minutes. The pH is then adjusted to 7.0 and the supernatant is discarded. The polymer is then washed with phosphate, buffered saline 0.01 M, - pH 7.2 and finally suspended in this buffer to yield at 5.0% w/v suspension. This yields a mixture of the poly hydroxy material (V) and the polymaleic ester material (VI).

Polyhydroxy polycarboxylic acid compositions where R=H, lower alkylene or lower alkoxy with 1 to 4 carbon atoms may be made according to the above steps, except the styrene maleic anhydride polymer is replaced with ethylene maleic anhydride polymer (e.g., "EMA-21" from Monsanto Chemical Co., St. Louis, Mo.); alpha-methyl-ethylene maleic anhydride polymer; or alpha-methoxyethylene maleic anhydride polymer, respectively.

Polyhydroxy polycarboxylic acid compositions having a cross linking moiety with two carbon atoms may be formed according to the above steps, except that the 1,3-diamino-2-hydroxypropaneis replaced with a diaminohydroxyethane, such as 1,2-diamino-1-hydroxyethane. Polyhydroxy polycarboxylic acid compositions in which the cross linking moiety has multiple hydroxyl groups may be formed according to the above steps by replacing the 1,3-diamino-2-hydroxy propane with 1,2-diamino-1,2-dihydroxyethane.

Polyhydroxy polycarboxylic acid compositions having a cross linking moiety with three carbon atoms having multiple hydroxyl groups may be formed according to the above steps, except that the 1,3-diamino-2-hydroxypropane is replaced with a 1,3-diamino-di- or 1,3-diamino-tri-hydroxypropane such as 1,3-diamino-1,2-dihydroxy-propane or 1,3-diamino-1,2,3-dihydroxypropane.

Polyhydroxy polycarboxylic acid compositions having a cross linking moiety with four carbon atoms may be formed according to the above steps, except that the 1,3-diamino-2-hydroxypropane is replaced with an alpha, omega-diamino-mono-hydroxy-n-butane, such as 1,4-diamino-3-hydroxybutane or 1,4-diamino-1-hydroxybutane. Polyhydroxy polycarboxylic acid compositions in which the cross linking moiety has more than one hydroxyl group may be formed by the above steps, except the alpha, omega-diamino-monohydroxy-n-butane is replaced with a 1,4-diamino-di-, 1,4-diamino-tri- or 1,4-diamino-tetra-hydroxybutane, such as 1,4-diamino-2,3-dihydroxybutane or 1,4-diamino-1-2-dihydroxybutane; 1,4-diamino-1,2,3-trihydroxybutane; and 1,4-diamino-1,2,3,4-tetrahydroxybutane.

EXAMPLE 2

Deesterification of Water-Insoluble Precipitating Agent (Mixture of Partially Esterified Material (VI)and Deesterified Material (V)

The polyhydroxy polycarbonyl mixed composition formed in Example 1 suspended in the buffer at a 5.0% weight/volume suspension, was centrifuged at 3000×g for 10 minutes and the suspending buffer discarded. The pellet was then dispersed in deionized water to yield a 5.0% w/v suspension. An equal volume of 0.2N aqueous sodium hydroxide solution was slowly added to the polymer suspension with stirring. The alkaline mixture was then allowed to stand at room temperature for 24 hours. Free base was then removed (in the supernate) by repeated centrifugation and washing with deionized water. The polymer was then equilibrated with 0.01M phosphate buffer pH 7.2 to yield a 5.0% w/v polymer suspension. This yields the polyhydroxy material (VI free of the polymaleic ester material (VI).

In accordance with the above procedure, the polymaleic ester material (VI) mixed with the polyhydroxy material (V) can be purified. This may be done with materials from the following sources.

Polyhydroxy polycarboxylic acid compositions where R=H, lower alkylene or lower alkoxy with 1 to 4 carbon atoms may be made according to the above steps, except the styrene maleic anhydride polymer is replaced with ethylene maleic anhydride polymer (e.g., "EMA-21" from Monsanto Chemical Co., St. Louis, Mo.); alpha-methyl-ethylene maleic anhydride polymer; or alpha-methoxyethylene maleic anhydride polymer, respectively.

Polyhydroxy polycarboxylic acid compositions having a cross linking moiety with one carbon atom may be formed according to the above steps except 1,3-diamino-2-hydroxypropane is replaced with a diaminohydroxymethane.

Polyhydroxy polycarboxylic acid compositions having a cross linking moiety with two carbon atoms may be formed according to the above steps, except that the 1,3-diamino-2-hydroxypropaneis replaced with a diaminohydroxyethane, such as 1,2-diamino-1-hydroxyethane. Polyhydroxy polycarboxylic acid compositions in which the cross linking moiety has multiple hydroxyl groups may be formed according to the above steps by replacing the 1,3-diamino-2-hydroxy propane with 1,2-diamino-1,2-dihydroxyethane.

Polyhydroxy polycarboxylic acid compositions having a cross linking moiety with three carbon atoms having multiple hydroxyl groups may be formed according to the above steps, except that the 1,3-diamino-2-hydroxypropane is replaced with a 1,3-diamino-di- or 1,3-diamino-tri-hydroxypropane such as 1,3diamino-1,2-dihydroxy-propane or 1,3-diamino-1,2,3-dihydroxypropane.

Polyhydroxy polycarboxylic acid compositions having a cross linking moiety with four carbon atoms may be formed according to the above steps, except that the 1,3-diamino-2-hydroxypropane is replaced with an alpha, omega-diamino mono-hydroxy-n-butane, such as 1,4-diamino-3-hydroxybutaneor 1,4-diamino-1-hydroxybutane. Polyhydroxy polycarboxylic acid compositions in which the cross linking moiety has more than one hydroxyl group may be formed by the above steps, except the alpha, omega-diamino-monohydroxy-n-butane is replaced with a 1,4-diamino-di-, 1,4-diamino-tri- or 1,4-diamino-tetra-hydroxybutane, such as 1,4-diamino-2,3-dihydroxybutane or 1,4-diamino-1-2-dihydroxybutane; 1,4-diamino-1,2,3-trihydroxybutane; and 1,4-diamino-1,2,3,4-tetrahydroxybutane.

EXAMPLE 3

The polyhydroxy polycarboxylic composition made according to Example 1 (V and VI) is evaluated for its ability to precipitate the diverse materials listed in Table 1 below. All the materials listed in Table 1 (from human serum albumin through plasmid DNA) are obtained in powder or particulate form from the Sigma Chemical Company, St. Louis, Mo.

Human serum albumin (HSA) is dissolved in 0.01 M sodium phosphate buffered 0.9% saline, having a pH 7.3–7.5 at a concentration of 33 mg/ml. (The remaining compounds; human gamma globulins through plasmid DNA, are similarly dissolved in an identical phosphate buffered saline at the concentrations indicated in Table 1. The isoelectric point (pI) as well as the percent carbohydrate (% Carb.) of each protein is indicated in Table 1.

A 5% weight/volume solution of the polyhydroxy polycarboxylic acid composition made in Example 1 is also made using the sodium phosphate buffered saline solution.

One volume of the cross-linked polyhydroxy polycarboxylic acid composition solution ("deproteinizing agent") is combined with 1, 2 or 4 equal volumes of the sample solution. Each combination of solutions is mixed by inversion then allowed to stand at room temperature for 5–15 minutes. Each solution is then centrifuged at 2,000×G for 10 minutes to remove the protein-polyhydroxy polycarboxylic acid composition matrix. The percent of protein removal from each remaining supernatant is measured by ultraviolet absorption (at 280 nm) or colorimetric determination (using the "BCA Protein Assay Reagent" from the Pierce Company, Rockville, Ill.) The percentage of protein removal ("% Removal") is indicated in Table 1 for each sample at all 3 volume combinations.

The proteins human serum albumin, human gamma globulins, hemoglobin, Transferrin and Cytochrome C, are all removed at levels of 90% or above by the cross-linked polyhydroxy polycarboxylic acid composition. These proteins have uniformly low levels of carbohydrate associated with them. By contrast, A1 acid glycoprotein, horseradish peroxidase and Fetuin each have substantial amounts of carbohydrate and therefore inferior "percent removal". Finally, as is seen with both DNA sample in Table I, non-proteinaceous materials are hardly precipitated at all by the cross-linked polyhydroxy polycarboxylic acid composition.

TABLE 1

| Sample | Sample Conc. (mg/ml) | pI | % Carbohydrate | Vol. of Deproteinizing Agent (VI) to Vol. of Sample (% Removal) | | |
|---|---|---|---|---|---|---|
| | | | | 1/1 | 1/2 | 1/4 |
| Reactive Compounds | | | | | | |
| Human Serum Albumin | 33 | 4.9 | | >99 | 99 | 90 |
| Human Gamma Globulins | 25 | 5–7 | 2–3 | >99 | 95 | 91 |
| Hemoglobin | 10 | 6.8 | | | >99 | 99 |
| Transferrin | 1 | 5.9 | 6 | | 95 | 92 |
| Cytochrome C | 2 | 10.6 | | | >99 | 99 |
| Unreactive Compounds | | | | | | |
| a1-Acid Glycoprotein | 1 | 2.7 | 41 | | 60 | 2 |
| Horseradish Peroxidase | 1 | 8.8 | 22 | | 23 | 2 |
| Fetuin | 1 | 3.5 | 22 | | 55 | 1 |
| Calf Thymus DNA | $A_{260}$ = 2.0 | | | <1 | <1 | <1 |
| Plasmid DNA | $A_{260}$ = 0.5 | | | <1 | <1 | <1 |

Note - These values were taken from isolated systems. For heterogeneous systems, selectivity will increase due to a competitive environment.

EXAMPLE 4

The tests of Example 3 were repeated at a concentration of 2.5% wt/vol suspension of the partially esterified polymer (VI) and deesterified polymer (V) prepared in accordance with Example 2.

TABLE 2

| | | Vol. of Deproteinizing Agent to Vol. of Sample (% Removal) | | | | | |
|---|---|---|---|---|---|---|---|
| | | Partially esterified (VI) + (V) | | | Deesterified (V) only | | |
| Sample | Conc. (mg/ml) | 1/1 | 1/2 | 1/4 | 1/1 | 1/2 | 1/4 |
| Reactive Compounds | | | | | | | |
| Human Serum Albumin | 33 | >99 | 85 | 60 | >99 | >99 | 96 |
| Human Gamma Globulins | 25 | >95 | 88 | 50 | >99 | 95 | 90 |
| Hemoglobin | 10 | >99 | 99 | 82 | >99 | >99 | >99 |
| Transferrin | 1 | 95 | 92 | 58 | >99 | 98 | 90 |
| Cytochrome C | 2 | >99 | >99 | 90 | >99 | >99 | >99 |
| Unreactive Compounds | | | | | | | |
| a1-Acid Glycoprotein | 1 | 60 | 2 | 0.5 | 65 | 4 | 1 |
| Horseradish Peroxidase | 1 | 20 | 2 | 0.5 | 24 | 2 | 1 |
| Fetuin | 1 | 45 | 1 | 0.5 | 51 | 1 | 1 |
| Calf Thymus DNA | $A_{260}$ = 2.0 | <1 | <1 | <1 | <1 | <1 | <1 |
| Plasmid DNA | $A_{260}$ = 0.5 | <1 | <1 | <1 | <1 | <1 | <1 |

EXAMPLE 5

Two solutions each of human serum albumin and human gamma globulins are made according to Example 3 (i.e., at 33 and 25 mg/ml. respectively, in 0.01M sodium phosphate buffered 0.9% saline at pH 7.3–7.5). There is also prepared a 5% weight/volume solution of cross-linked polyhydroxy polycarboxylic acid composition made according to Example 1.

The first human serum albumin and human gamma globulin solutions are maintained at room temperature (approximately 20° C.) and the second of each of these solutions are heated to and kept at 60° C. The cross-linked polyhydroxy polycarboxylic acid composition solution is then added to each of the four protein solutions in a ¼ volume of "deproteinizing agent" to volume of protein sample.

The results of the protein removal efficiency measured as in Example 2, appear below in Table 3.

TABLE 3

| Sample | % Removal |
|---|---|
| Human Serum Albumin - 20° C. | 90 |
| Human Serum Albumin - 60° C. | greater than 99 |
| Human Gamma globulin - 20° C. | 91 |
| Human Gamma globulin - 60° C. | greater than 99 |

EXAMPLE 6

The experiment of the foregoing Example 5 was repeated using the deesterified agent (V) produced in Example 2 at a polymer concentration of 2.5% wt/vol, The polymer to sample ratio was ⅕. The results are summarized in Table 4 below.

TABLE 4

| Sample | % Removal |
| --- | --- |
| Human Serum Albumin - 20° C. | 80 |
| Human Serum Albumin - 30° C. | 90 |
| Human Serum Albumin - 60° C. | greater than 99 |
| Human Gamma Globulin - 20° C. | 82 |
| Human Gamma globulin - 30° C. | 94 |
| Human Gamma globulin - 60° C. | greater than 99 |

I claim:

1. A water insoluble cross-linked polyhydroxy polycarboxylic acid obtained by cross-linking a polymer of the formula:

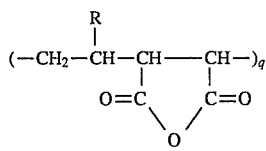

wherein R is hydrogen or lower alkylene or lower alkoxy of 1–4 carbon atoms, or phenyl, and q is an integer of 7 to 10,000, with an alpha, omega diaminohydroxy alkane of the formula:

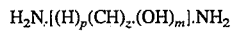

wherein z is an integer of 1–4, p is 0 or an integer up to z–1, m is 1 or an integer up to z, and hydrolyzing the unreacted anhydride groups, wherein the ratio of the initially charged diaminohydroxyalkane to the initially charged poly (alkylene maleic anhydride) is between about 1 and about 200 to 1 mol/mol, said water insoluble cross-linked polyhydroxy polycarboylic acid being selected from the group consisting of such acids having at least two strands each having a strand skeleton of formula III:

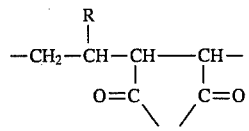

wherein one carbonyl group of at least one maleoyl moiety thereof in each strand is covalently linked to a

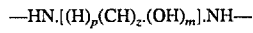

moiety to provide the presence therein of cross linking moieties of the formula:

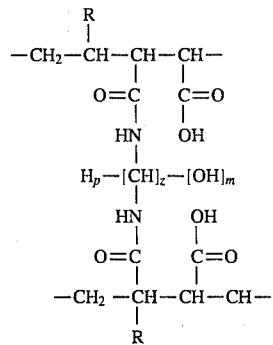

and

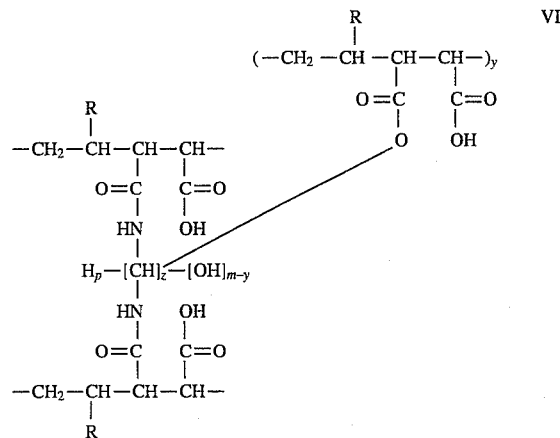

wherein R, z, p and m are as defined above, and y is an integer up to m, and the esters thereof with the anhydride corresponding to the skeleton of formula III, wherein the ratio of cross-links to poly (alkylene carbonic acid) strands is between about 1 and about 200 to 2.

2. The product obtained by treatment of the water insoluble cross-linked polyhydroxy polycarboxylic acid of claim 1 with aqueous alkali.

3. A water insoluble cross-linked polyhydroxy polycarboxylic acid having at least two strands each having a strand skeleton of formula III:

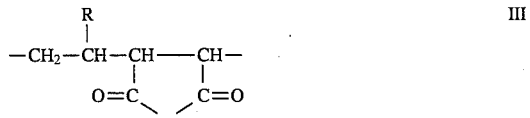

wherein one carbonyl group of at least one maleoyl moiety thereof in each strand is covalently linked to a

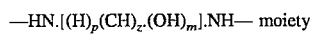

to provide the presence therein of cross linking moieties of the formula:

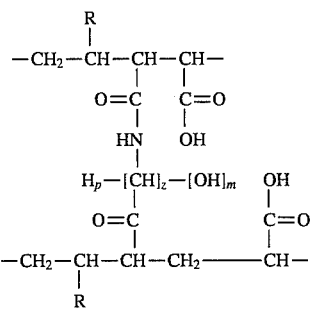

and

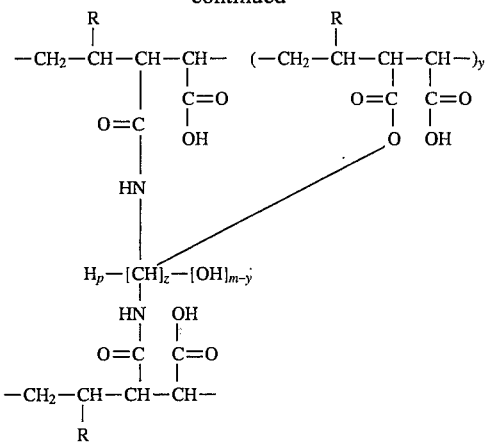

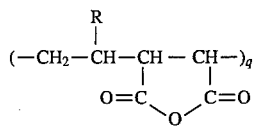

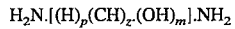

wherein R is hydrogen of lower alkylene or lower alkoxy of 1–4 carbon atoms, or phenyl, y is an integer up to m, z is an integer of 1–4, p is 0 or an integer up to z–1, m is 1 or an integer up to z, and the esters thereof with the anhydride corresponding to the skeleton of formula III, wherein the ratio of cross-links to poly (alkylene carbonic acid) strands is between about 1 and about 200 to 2.

4. A method of making insoluble cross-linked polyhydroxy polycarboxylic acid containing of claim 1 which compromises a) cross-linking a polymer of the formula:

wherein R is hydrogen or lower alkoxy or lower alkylene of 1–4 carbon atoms, or phenyl, q is an integer of 7 to 10,000, with an alpha, omega diaminohydroxy alkane of the formula:

$$H_2N.[(H)_p(CH)_z.(OH)_m].NH_2$$

wherein z is an integer of 1–4, p is 0 or an integer up to z–1, m is 1 or an integer up to z, and b) hydrolyzing the unreacted anhydride groups, wherein the ratio of initially charged diaminohydrxyalkane to initially charged poly (alkylene maleic anhydride) is between about 1 and about 200 to 1 mol/mol.

5. A method of hydrolyzing the water insoluble cross-linked polyhydroxy polycarboxylic acid compound of Formula VI of claim 3 which compromises treating said compound of Formula VI with dilute aqueous alkali.

* * * * *